(12) United States Patent
Florentino, Jr.

(10) Patent No.: US 7,458,167 B2
(45) Date of Patent: Dec. 2, 2008

(54) ARM ANGLE INDICATOR

(75) Inventor: Michael Florentino, Jr., Ocean Grove, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 660 days.

(21) Appl. No.: 11/026,144

(22) Filed: Dec. 30, 2004

(65) Prior Publication Data

US 2006/0149288 A1 Jul. 6, 2006

(51) Int. Cl.
*A61B 5/103* (2006.01)
(52) U.S. Cl. ......................................... 33/512; 600/587
(58) Field of Classification Search .................. 33/1 N, 33/285, 512; 600/587, 595
See application file for complete search history.

(56) References Cited

U.S. PATENT DOCUMENTS

| | | | | | |
|---|---|---|---|---|---|
| 1,590,499 | A * | 6/1926 | Cozag | .......................... | 600/595 |
| 4,719,925 | A * | 1/1988 | Parsons | ....................... | 33/512 |
| 4,940,063 | A * | 7/1990 | Challis | ........................ | 600/587 |
| 4,989,337 | A * | 2/1991 | Mason et al. | ................. | 33/512 |
| 5,070,623 | A * | 12/1991 | Barnes | ......................... | 33/512 |
| 5,188,121 | A * | 2/1993 | Hanson | ....................... | 600/595 |
| 5,376,093 | A * | 12/1994 | Newman | ..................... | 606/88 |
| 5,457,891 | A * | 10/1995 | Taylor | .......................... | 33/512 |
| 5,593,448 | A | 1/1997 | Dong | | |
| 5,776,082 | A * | 7/1998 | Riley et al. | ................. | 600/595 |
| 5,792,077 | A * | 8/1998 | Gomes | ........................ | 600/595 |
| 5,911,695 | A * | 6/1999 | Watkins et al. | ............... | 600/587 |
| 6,361,506 | B1 * | 3/2002 | Saenger et al. | ............... | 600/587 |
| 6,790,234 | B1 | 9/2004 | Frankle | | |
| 6,872,187 | B1 * | 3/2005 | Stark et al. | ................... | 600/587 |
| 2002/0143277 | A1 * | 10/2002 | Wood et al. | .................. | 600/595 |
| 2004/0107592 | A1 * | 6/2004 | Matlis | .......................... | 33/512 |
| 2007/0276296 | A1 * | 11/2007 | Bright et al. | ................. | 600/595 |

OTHER PUBLICATIONS

Surgical Protocol, "Solar Total Shoulder System", Stryker Osteonics: The science of Better Fit, Mar. 1998.
Bi-Angular Shoulder System, "Surgical Technique", Biomet Orthopedics Inc, 2003.
Global Advantage Shoulder Anthroplasty System, "Surgical Technique", Depuy, 2000.
Reverse Shoulder Prosthesis, "Surgical Techniques", Encore, Jun. 2005.
Zimmer, Biagliani/Flatow The Complete Shoulder Solution, "Total Shoulder Arthroplasy Surgical Technique", 2003.

* cited by examiner

*Primary Examiner*—G. Bradley Bennett
(74) *Attorney, Agent, or Firm*—Lerner, David, Littenberg, Krumholz & Mentlik, LLP

(57) ABSTRACT

An angle measurement device is provided for determining the version angle for the prosthetic humeral head during shoulder replacement surgery. The device has a first collar for contacting the forearm and has a first coupling element in the form of a rod aligned with the ulna. The device has a second collar for contacting the upper arm when the elbow is flexed to 90°. The second collar has a second coupling element coupled thereto extending in a direction generally perpendicular to the humerus. The second coupling element is pivotally coupled to the first coupling element for rotation about a pivot point axis. An angle indicator having angle indicia is located at said pivot point and fixed to one of said first or second arm contacting collars for indicating the angle between the ulna and the humerus during external rotation of the forearm.

22 Claims, 6 Drawing Sheets

ARM ANGLE INDICATOR

BACKGROUND OF THE INVENTION

This invention relates to an extramedullary angle indicator, i.e. goniometer for measuring the version angle of the humeral head. The version angle is then used to orient a humeral prosthesis in the canal of the humerus.

One of the most critical steps in successful shoulder replacement is determining and maintaining the version of the humeral head. Most surgical techniques for total shoulder replacement advise the surgeon that the humeral component should be set at approximately 30-40° of retroversion. This will restore the shoulder's range of motion and the overall stability of the joint. Although the recommendations for humeral head retroversion are similar in most shoulder surgeries, the method in which this version is measured varies.

A prior art technique developed by Stryker Corp. for their Solar™ total shoulder, as shown in FIG. 1, instructs the surgeon to flex the patient's elbow 90° and externally rotate the forearm 30-40°.

In this system, as shown in FIG. 1, the surgeon uses the patient's sagittal plane (90° arrow) as a zero reference while rotating the forearm 30-40° away from the body. At this point, the surgeon visually sets the forearm at 30-40° and thereafter makes the humeral head resection in a known manner (not shown). The humeral head resection cut is made at right angles to the plane of the humeral shaft and head, thereby achieving 30-40° of retroversion.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body. The sagittal plane is a vertical plane running from head to toe and dividing the body into right and left sections. The frontal or coronal plane is a vertical plane dividing the body into front and back sections.

SUMMARY OF THE INVENTION

It is one aspect of the invention to provide an instrument capable of measuring the version angle of the head of the humerus in a patient's shoulder joint.

It is yet another aspect of the invention to provide a instrument which connects to the forearm and to the upper arm via a pivotal connection which includes an angle measuring portion such as a distal face with angle markings and a locking portion so that the surgeon can dial in a selected version angle.

These and other aspects of the invention are provided by an arm angle measurement and indication device for determining the version angle of the humeral head during shoulder replacement surgery. The angle measurement device includes a first element in the form of a collar for contacting the forearm with the elbow flexed to 90°, and a second element also in the form of a collar for contacting the upper arm. The first element has a coupling element such as an L-shaped rod having a first link extending in a direction perpendicular to the forearm and a second link extending in a direction generally parallel to the axis of the forearm, thus forming the L-shaped configuration. The second element includes a coupling element, for example, in the form of a short rod which extends generally perpendicular to the axis of the upper arm, i.e. the humerus. The links of the first and second element are pivotally connected at a pivot point with a pivot axis extending, when the elbow is at 90°, in an inferior-superior direction along a plane parallel to both the sagittal plane and the frontal plane. An angle indicator having angle indicia located thereon centered at the pivot point is fixed to one of the first or second elements for indicating the angle between the first and second coupling elements for various external rotational position of the forearm with respect to the upper arm.

The angle indicator has a dial face with angle indicia from ±40° preferably at 5° increments centered about the pivot point. The 0° point is the position where the axis of the forearm or ulna and the humerus are in a plane parallel to the sagittal plane. V-shaped detents are provided on the edge of the dial.

The angle indicator is preferably mounted on the second element, i.e. the element for connecting to the upper arm. A spring loaded locking element is slidably mounted on the L-shaped arm connected to the first element, i.e. the element connected to the forearm and is biased into engagement with the detents on the angle indicator. The detents may be recesses in the dial face which recesses are preferably located at 5° increments ±40° on either side of the 0 point.

The first and second elements are preferably in the form of semi-circular collars having posterior open ends which fit over the forearm and upper arm in the bicep area. Straps may be included on the collars for positively coupling them to the arms.

BRIEF DESCRIPTION OF THE DRAWINGS

The present invention will be better understood on reading the following detailed description of non-limiting embodiments thereof, and on examining the accompanying drawings, in which:

FIG. 10 is the arm angle indicator of the present invention mounted on an arm where the forearm is retroverted between 30° and 40° from the sagittal plane.

DETAILED DESCRIPTION

Figure 1:
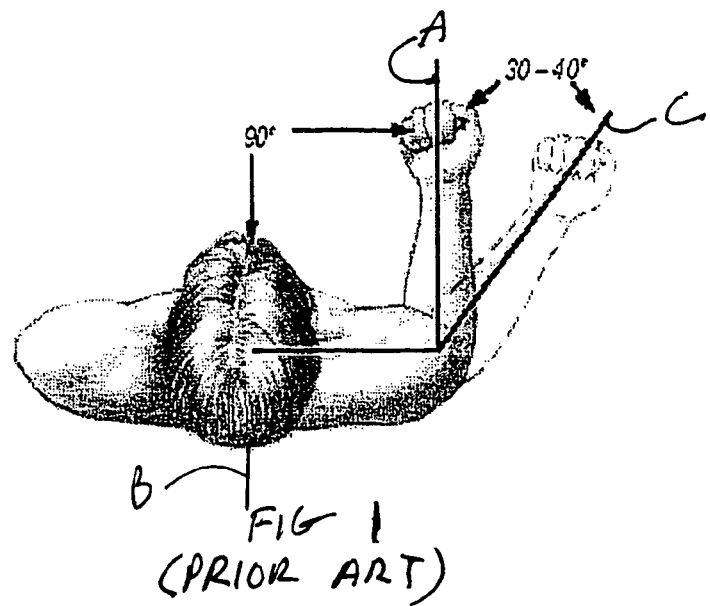
FIG. 1 is a view of a patient looking down on the patient's head showing the prior art method with the patient's arm being rotated from a position parallel to the sagittal plane to a position 30-40 of retroversion with respect to the shoulder joint.
Figure 2:
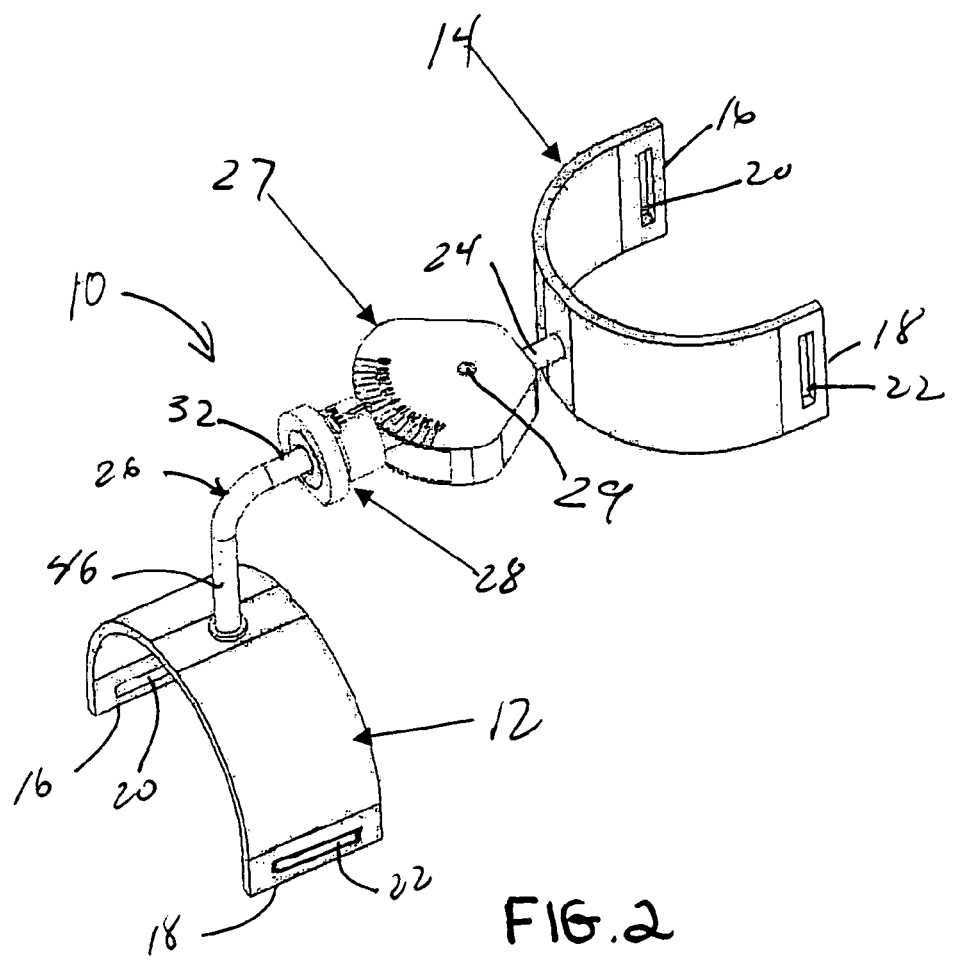
FIG. 2 is a perspective view of the arm angle indicator of the present invention.
Figure 3:
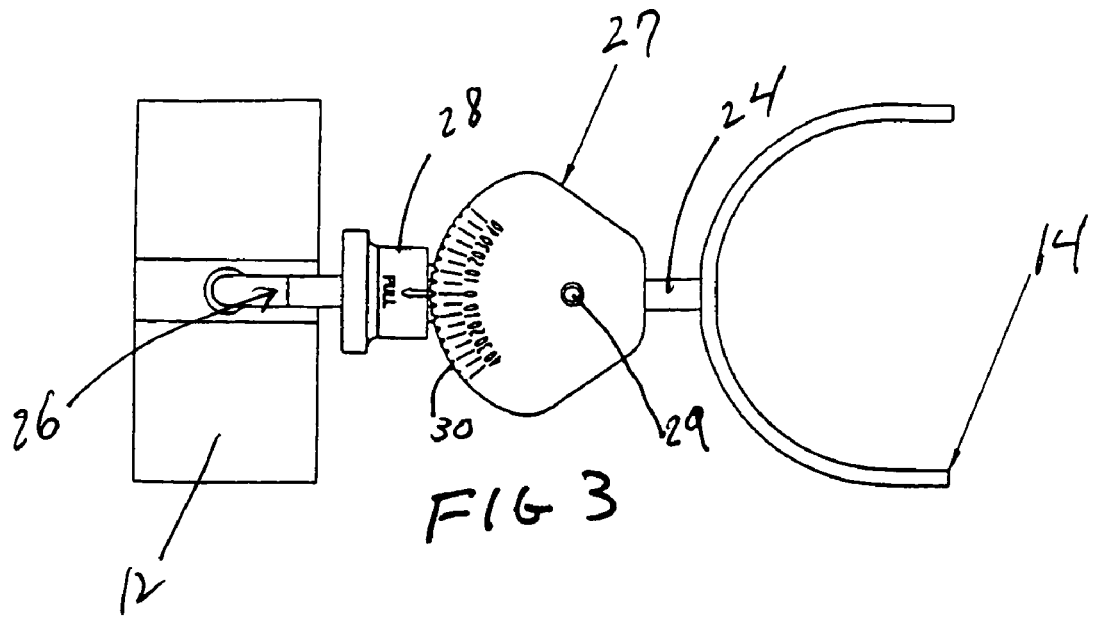
FIG. 3 is a top view of the arm angle indicator shown in FIG. 1.
Figure 4:
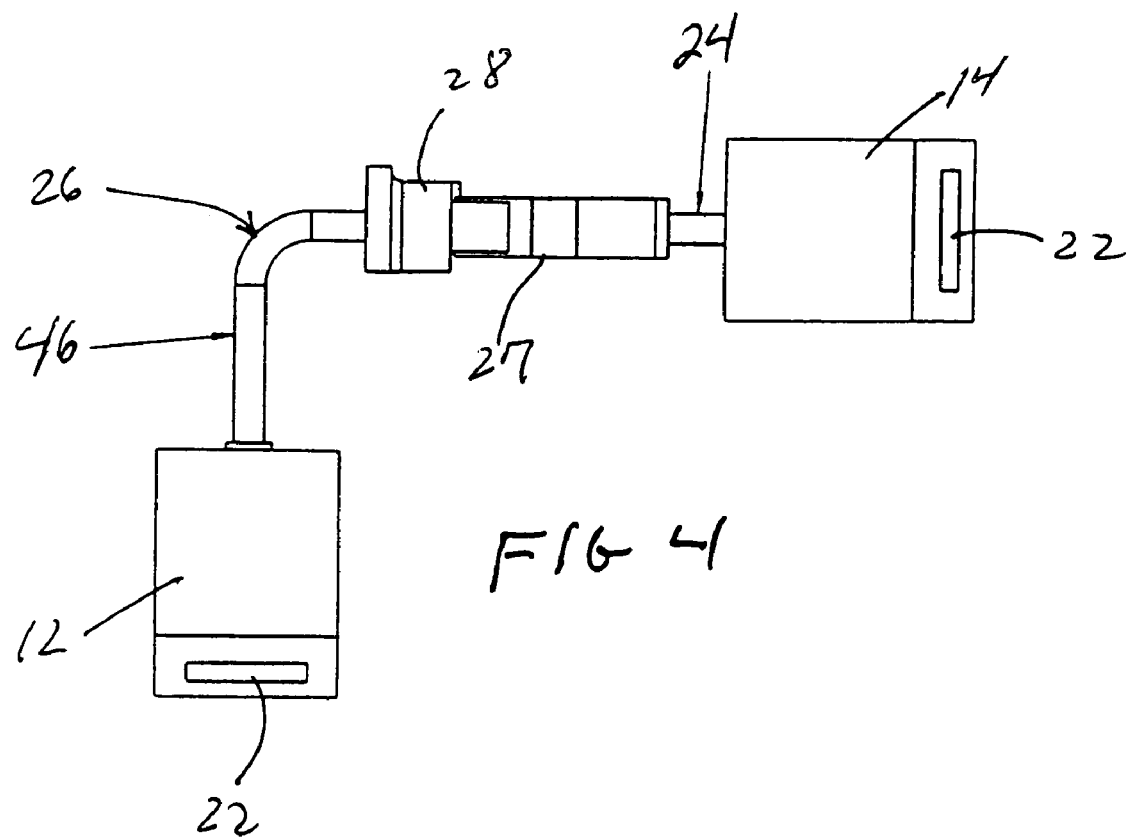
FIG. 4 is a side elevation view of the arm indicator of FIG. 3.
Figure 5:
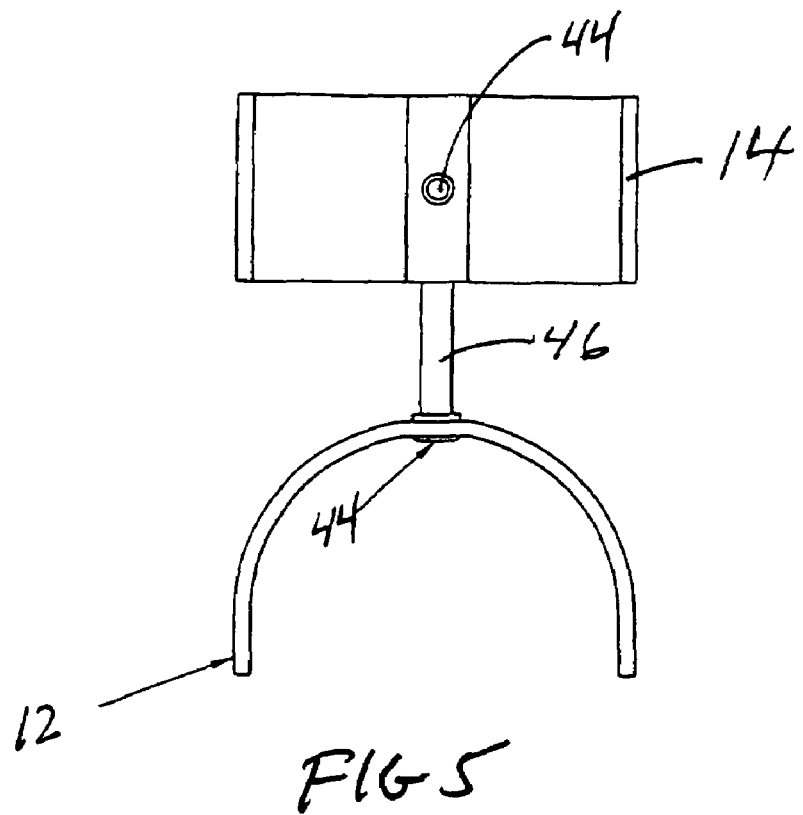
FIG. 5 is an end view of the arm angle indicator of FIG. 4 from the right side thereof.

Referring to FIG. 1, there is shown a prior method of setting the version angle with a patient viewed from above, having his forearm placed in a first position A where the forearm is parallel to the sagittal plane B and rotated to a second position C where the forearm position causes the humerus to be retroverted between 30 and 40° with respect to the shoulder glenoid. Referring to FIG. 2, there is shown the angle indicator of the present invention generally denoted as 10 having a first collar element 12 for coupling to the forearm and a second element 14 for coupling to the upper arm in the bicep area. In the preferred embodiment, each collar 12, 14 is generally semi-circular and includes ends 16 and 18 which include slots 20 and 22 for receiving straps not shown. The straps are designed to couple to ends 16 and 18 through slots 20 and 22 and wrap around either the forearm or the upper arm. The straps may be held in position by Velcro fastening systems coupled to each end of a separate strap. Thus, with the elbow at 90°, when the pair of straps coupled to collar 12 are wrapped around the forearm and the pair of straps coupled to collar 14 are wrapped around the upper arm, the angle indicator is snuggly mounted externally of the arm.

Figure 8:
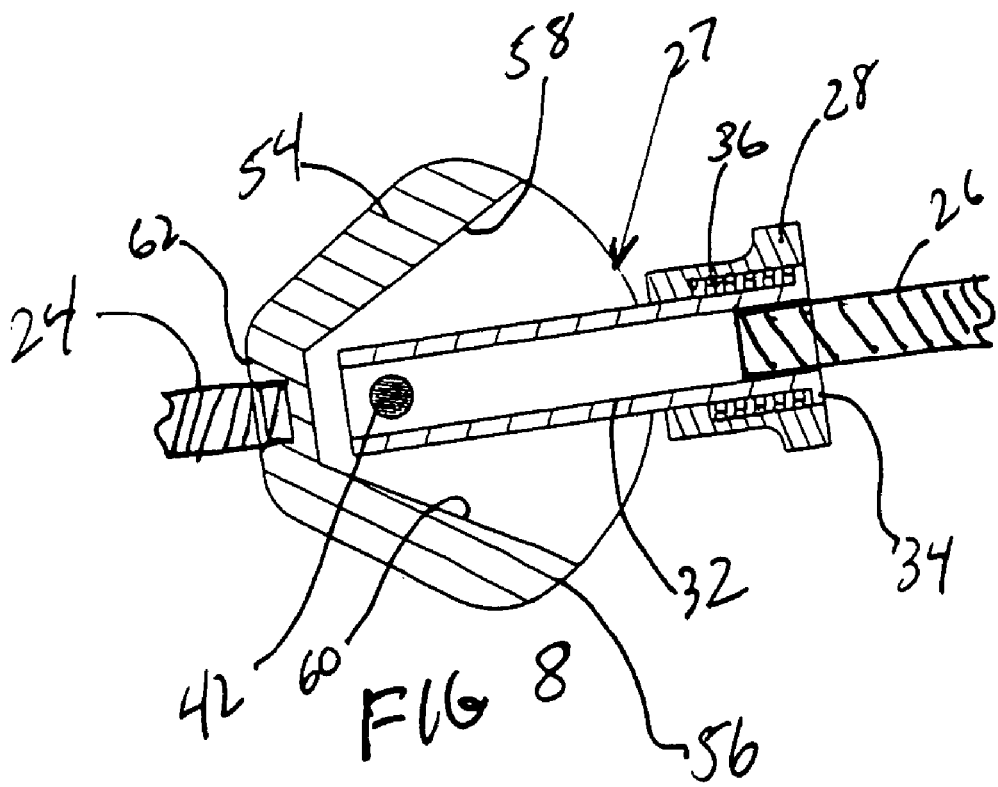
FIG. 8 is a cross-sectional view of FIG. 6 along lines 8-8.
Figure 7:
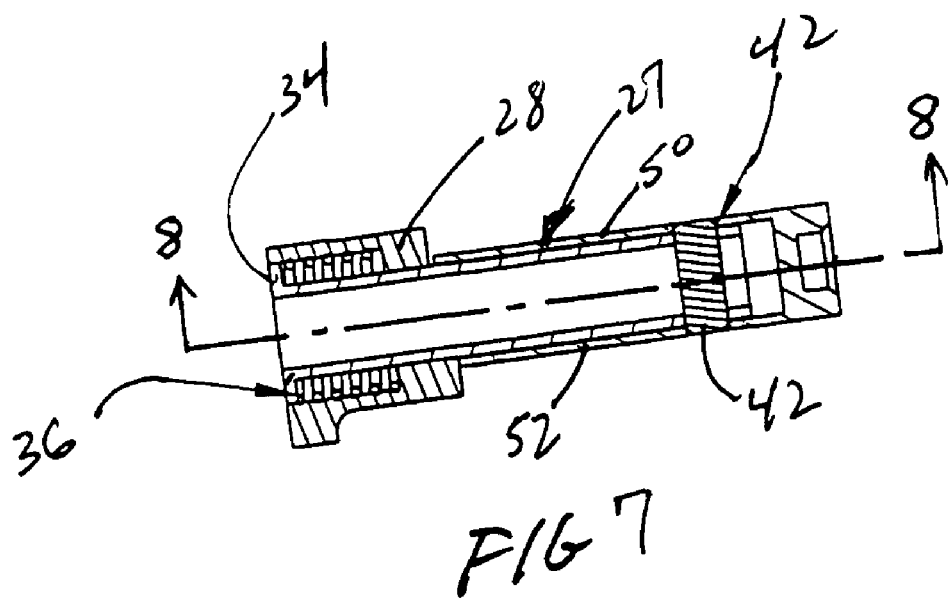
FIG. 7 is a cross-sectional bottom view of FIG. 6.

Collar element 14 includes a post 24 rigidly coupled thereto preferably at the center of the strap between ends 16 and 18. Likewise, collar element 12 includes a post 26 coupled to collar 12 intermediate ends 16 and 18 thereof. In the preferred embodiment, post 24 is rigid and straight whereas post 26 is L-shaped having a 90° bend and has a locking element 28 mounted thereon. Referring to FIGS. 7 and 8, it can be seen that post 26 includes an extension portion 32 which extends within angle indicator 27 and is pivotally coupled to pivot pin 29. Preferably, pin 29 extends through indicator 27 in a direction perpendicular to the axis of the ulna when the elbow is at 90°.

Referring to FIGS. 3-7, it can be seen that angle indicator 27 has numbered angle indications of ±40° in 10° increments along curved portion 30 of angle indicator 27 with 5° marking lines intermediate the 9 numbers. Curved surface 30 has its center at pivot pin 29. An annular angle locking element 28 is moveable along a first link 32 of angled rod 26 and is spring biased into engagement with surface 30 of angle indicator 27. As can be seen in FIGS. 7 and 8, end portion 32 of rod 26 can be formed as a separate piece fixably attached to rod 26. End portion 32 has a flange 34 at the end thereof adjacent rod 26 ands supports locking element 28 which is slidably mounted on the outer surface of portion 32. Slidable locking element 28 is spring biased into engagement with outer curved surface 30 of angle indicator 27 by spring 36. Spring 36 surrounds the outer surface of portion 32 and has a first end engaging flange 34 and a second end engaging an annular inner surface on locking element 28. Since flange 34 is integral with portion 32, locking element 28 is spring biased into engagement with surface 30 of indicator 27.

Figure 6:
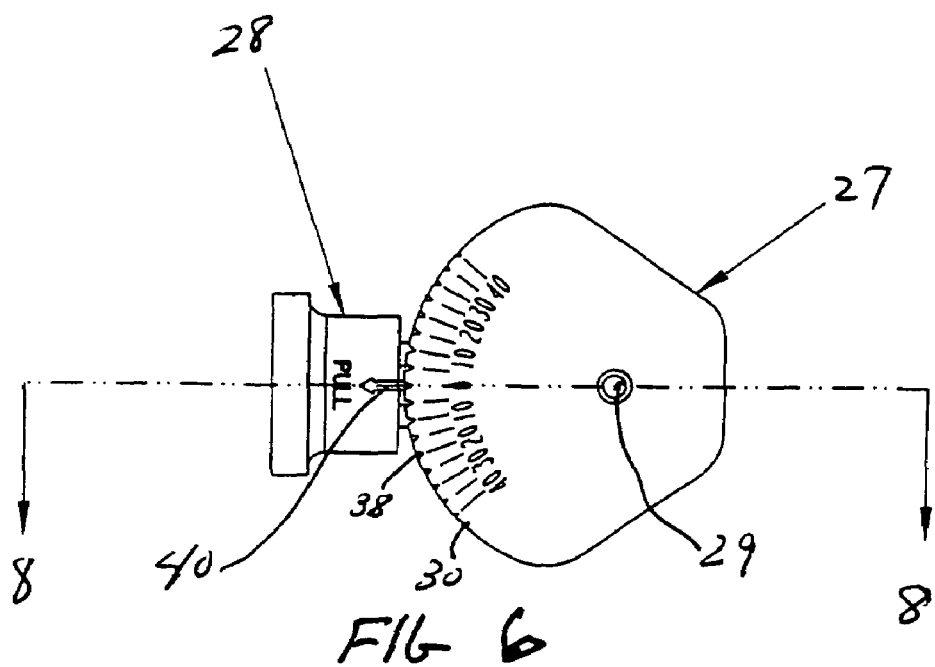
FIG. 6 is a plan view of the pivot point dial and locking element of the arm angle indicator of the present invention.

In the preferred embodiments, surface 30 includes a plurality of generally V-shaped indented portions 38 which can be best seen in FIG. 6. In the preferred embodiment, each indented portion 38 corresponds to a 5° increment in either direction about the 0 point, i.e. the point where the forearm is parallel to the sagittal plane through the body. In the preferred embodiment, locking element 28 includes a V-shaped nose portion 40 which engages a corresponding V-shaped indentation 38 to lock extension 32 and rod 26 in a desired angular position.

As shown in the figures, extension 32 and rod 26 are pivotally coupled within angle indicator 27 at pivot point 29 by a preferably cylindrical pivot pin 42 shown best in FIG. 7. In the preferred embodiment, rod 26 is fixedly coupled to collar 12 in any convenient manner such as a rivet 44 shown in FIG. 5 or by having a screw threaded through the wall of collar 12 into a threaded hole in lower portion 46 of rod 26. In the preferred embodiment, a similar coupling system is used to couple collar 14 to rod 24.

As best seen in FIGS. 2, 7 and 8, the preferred angle indicator 27 has two spaced apart upper and lower walls 50 and 52. In the preferred embodiment, these walls are spaced a distance equal to or slightly greater than the outer diameter of extension 32 of rod 26. As can be seen in FIG. 8, angle indicator 27 has outer walls 54 and 56 which have V-shaped inner surfaces 58 and 60 which act as stops or limits for the angular rotation of extension 32 of rod 26 within angle indicator 27. As shown in FIG. 8, rod 24 is coupled to end 62 of angle indicator 27 in any convenient manner such as by being threaded into a threaded bore in end 62 or in a permanent manner such as by welding rod 24 to end 62. It would also be possible to eliminate rod 24 and attach the angle indicator directly to collar 14.

Figure 9:
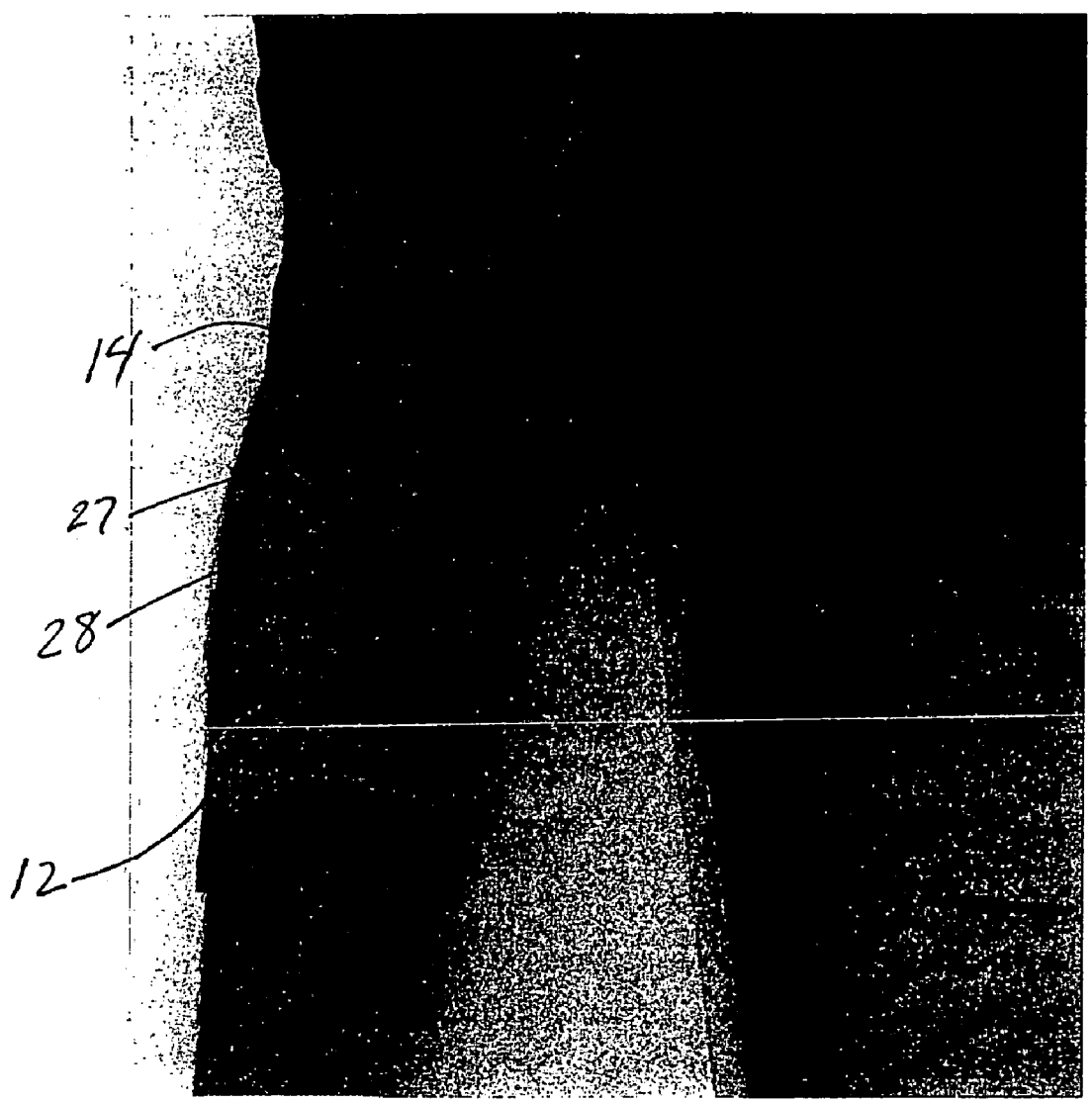
FIG. 9 is a view of the arm angle indicator on a right arm flexed to 90° with the forearm aligned with the sagittal plane.
Figure 16:
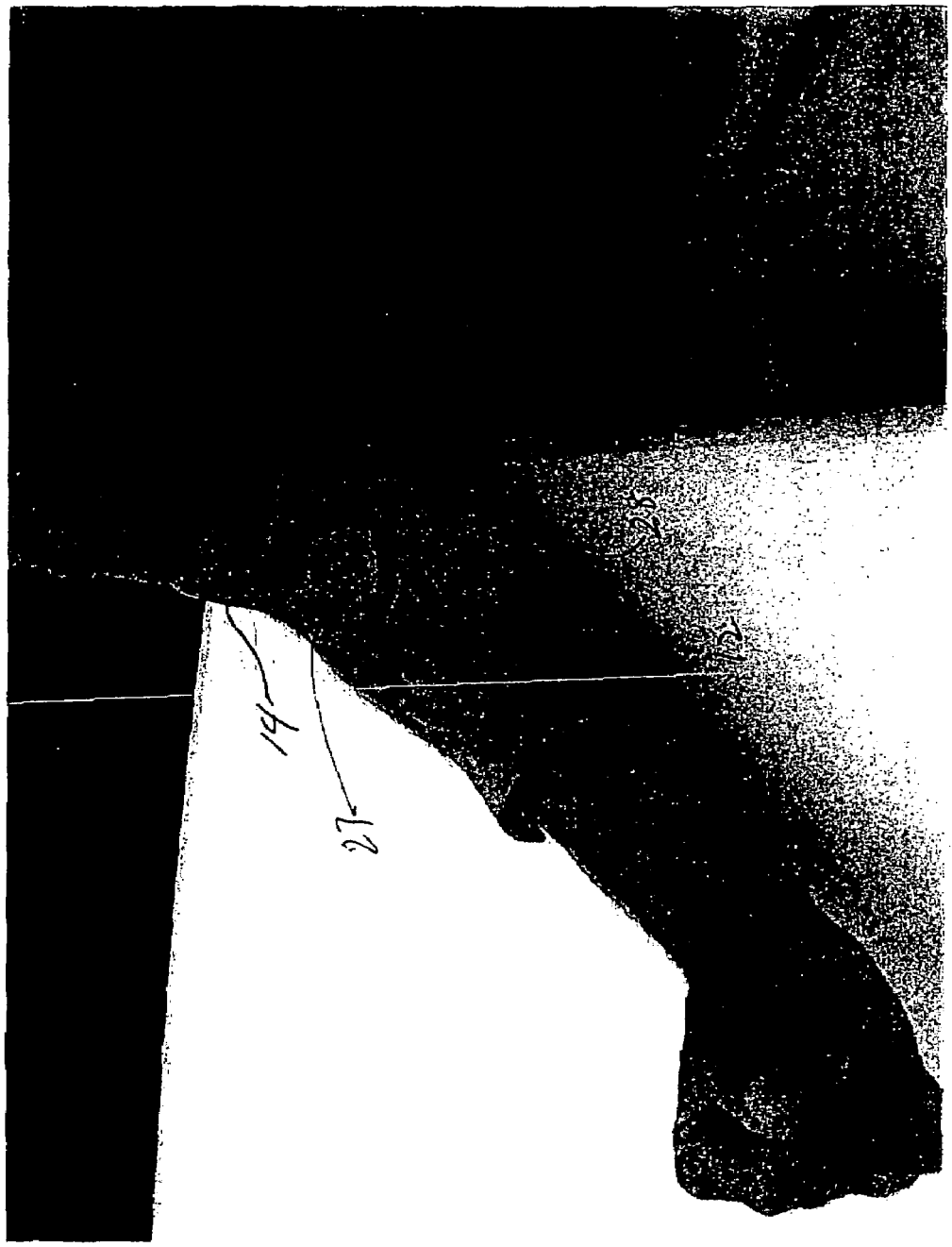

Referring to FIGS. 9 and 10, there is shown the arm angle indicator mounted on a patient's upper right arm (bicep area) and forearm. As shown, collar 12 engages the forearm and collar 14 engages the upper arm. In FIG. 9, the angle indicator is shown in the 0 position with the forearm position parallel to the sagittal plane. In FIG. 10, the forearm is externally rotated to between 30 and 40° to properly measure the version angle required for a prosthetic humeral implant with regard to the patient's right shoulder. The arm angle indicator 10 allows the surgeon to "dial in" the version of the humeral head. The same arm angle indicator can be used with the left arm with the 0° to 40° on the opposite side of 0° being used during external rotation of the left arm. Thus, the placement of the angle indications of between 5 and 40° on both sides of the 0° reference allows the arm angle indicator 10 to be used on the both left and right shoulder since, in all cases, the forearm is externally located as shown in FIG. 1. Incorporating the arm angle indicator 10 into the surgical procedure allows the surgeons to accurately and consistently set the version of the humeral components. Specifically, after the shoulder incision is made, the rotator interval and the anterior capsule are exposed. The capsulotomy is completed and the humeral head delivered for visualization and the articular surface defined using the arm angle indicator. The following instructional steps make up the goniometer or arm angle indicator. Attach collar 14 to bicep and collar 12 to forearm using supplied straps as shown in FIG. 9. Pull release knob 28 and externally rotate the forearm as specified in the prosthetic shoulder surgical protocol to the position for example of FIG. 10. Using the goniometer scale 30 dials the rotation of the forearm and releases the locking knob to lock the forearm in position. Once the rotation is set, continue to follow the prosthetic shoulder surgical protocol. Once the margin of the articular surface is determined, a humeral resection guide, (not shown), is placed on the humeral shaft and the rest of the surgical protocol is completed in the standard manner.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An arm angle measurement device for determining the version angle of the humeral head during shoulder surgery when the forearm is externally rotated with the elbow flexed to 90° comprising:

a first element for contacting the forearm having a first coupling element aligned with the ulna;

a second element for contacting the upper arm, said second element having a second coupling element aligned with to the humerus, said second coupling element pivotally coupled to said first coupling element for rotation about a pivot point; and an angle indicator having angle indicia located at said pivot point and fixed to one of said first or second elements for indicating the external rotation angle between said first and second coupling elements, wherein the external rotation angle is indicative of the version angle of the humeral head.

2. The angle measurement device as set forth in claim 1 wherein said angle indicator has a face with angle indicia from ± 40° centered about a position wherein the axis of the ulna is in a plane parallel to the sagittal plane.

3. The arm angle measurement device as set forth in claim 2 further comprising means for locking the first and second coupling element at a selected angle of said angle indicator.

4. The arm angle measurement device as set forth in claim 1 further comprising means for locking the first and second coupling element at a selected angle of said angle indicator.

5. The arm angle measurement device as set forth in claim 1 wherein the first and second elements are connected to the forearm and upper arm by collars which have open portions which are open to the posterior.

6. The arm angle measurement device as set forth in claim 5 wherein said open portions are oriented in generally perpendicular directions.

7. The arm angle measurement device as set forth in claim 5 wherein the collars are part circular with sectors open to the posterior for receiving the forearm and upper arm.

8. The arm angle measurement device as set forth in claim 7 wherein the collars are adapted to receive straps for respectively encompassing posterior portions of the forearm and upper arm.

9. The arm angle measurement device as set forth in claim 1 wherein the angle indicator is fixed to the second element.

10. The arm angle measurement device as set forth in claim 1 wherein the first and second elements have arm receiving portions oriented in generally perpendicular directions.

11. The arm angle indicator as set forth in claim 1 wherein said first and second coupling elements are rods extending from said first and second elements.

12. An angle indicator for displaying the external rotation angle between a 90° flexed forearm and upper arm with respect to the sagittal plane comprising:

a first collar shaped to receive the forearm;

a second collar shaped to receive the upper arm pivotally coupled to said first collar at a pivot point;

a dial adjacent said pivot point having angle indicia thereon for displaying the angle between said first and second collars about said pivot point; and means for locking said first and second collars at a selected angle, wherein the angle indicia indicates an angle corresponding to a version angle of the humeral head.

13. The angle measurement device as set forth in claim 12 wherein said dial has a face with angle indicia from ±40° centered about a position where the flexed ulna is in a plane parallel to the sagittal plane.

14. The angle measurement device as set forth in claim 12 wherein the first and second collars which have open portions which are open to the posterior.

15. The angle measurement device as set forth in claim 14 wherein said open portions are oriented in generally perpendicular directions.

16. The angle measurement device as set forth in claim 14 wherein the first and second collars are part circular with sectors open to the posterior for receiving the forearm and upper arm.

17. The angle measurement device as set forth in claim 16 wherein the first and second collars are adapted to receive straps for respectively encompassing posterior portions of the forearm and upper arm.

18. The angle measurement device as set forth in claim 12 wherein the dial is fixed to the second element.

19. The angle measurement device as set forth in claim 18 wherein said dial has a face with angle indicia from ±40° centered about a position where the ulna and humerus are coplanar with a plane parallel to the sagittal plane.

20. The angle measurement device as set forth in claim 12 wherein said first collar has an arm extending therefrom mounted to a pivot pin at said pivot point.

21. The angle measurement device as set forth in claim 20 wherein said dial is fixedly coupled to said second collar.

22. The angle measurement device as set forth in claim 21 wherein said means for locking said first and second collars at a selected angle include a spring loaded locking element slidably mounted on said arm.

\* \* \* \* \*